(12) United States Patent
Kim et al.

(10) Patent No.: US 9,085,674 B2
(45) Date of Patent: Jul. 21, 2015

(54) SILANE COMPOUND, METHOD FOR PREPARING THE SAME AND POLYCARBONATE RESIN COMPOSITION COMPRISING THE SAME

(71) Applicant: Samsung SDI Co., Ltd., Yongin-si (KR)

(72) Inventors: Yong Tae Kim, Uiwang-si (KR); Ha Na Ra, Uiwang-si (KR); Joong In Kim, Uiwang-si (KR); Su Hak Bae, Uiwang-si (KR); Ji Hye Lee, Uiwang-si (KR); Hyun Ho Lee, Uiwang-si (KR); Hyun Joo Han, Uiwang-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 14/537,219

(22) Filed: Nov. 10, 2014

(65) Prior Publication Data

US 2015/0148472 A1 May 28, 2015

(30) Foreign Application Priority Data

Nov. 22, 2013 (KR) ........................ 10-2013-0143093

(51) Int. Cl.
*C07F 7/02* (2006.01)
*C08K 5/548* (2006.01)
*C08K 3/34* (2006.01)

(52) U.S. Cl.
CPC .. *C08K 5/548* (2013.01); *C08K 3/34* (2013.01)

(58) Field of Classification Search
None
See application file for complete search history.

(56) References Cited

U.S. PATENT DOCUMENTS

| 3,364,246 | A | * | 1/1968 | Rossmy | 556/450 |
| 4,203,914 | A | * | 5/1980 | Finke et al. | 556/428 |
| 2005/0038145 | A1 | | 2/2005 | Gallucci et al. | |
| 2011/0003249 | A1 | * | 1/2011 | Bradford et al. | 430/270.1 |
| 2012/0245262 | A1 | | 9/2012 | Hao et al. | |

FOREIGN PATENT DOCUMENTS

EP    1860145 A1    11/2007

* cited by examiner

*Primary Examiner* — Robert S Loewe
(74) *Attorney, Agent, or Firm* — Additon, Higgins & Pendleton, P.A.

(57) ABSTRACT

A polycarbonate resin composition includes a polycarbonate resin; an inorganic filler, wherein the inorganic filler includes talc; and a novel silane compound represented by Formula 1:

[Formula 1]

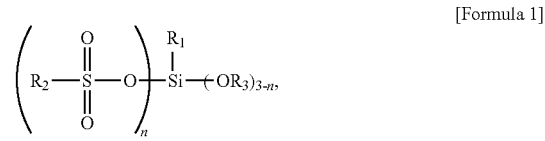

wherein $R_1$ is $C_6$ to $C_{30}$ alkyl, $R_2$ is a $C_6$ to $C_{30}$ hydrocarbon group, $R_3$ is hydrogen or $C_1$ to $C_5$ alkyl, and n has an average value from about 0.1 to about 3. The polycarbonate resin composition can have excellent impact resistance with minimal or no reduction in molecular weight of the polycarbonate resin.

12 Claims, No Drawings

SILANE COMPOUND, METHOD FOR PREPARING THE SAME AND POLYCARBONATE RESIN COMPOSITION COMPRISING THE SAME

CROSS-REFERENCE TO RELATED APPLICATION

This application claims priority under 35 USC Section 119 to and the benefit of Korean Patent Application No. 10-2013-0143093, filed Nov. 22, 2013, the entire disclosure of which is incorporated herein by reference.

FIELD OF THE INVENTION

The present invention relates to a silane compound, a method for preparing the same, a polycarbonate resin composition including the same, and a molded article comprising the resin composition.

BACKGROUND

When a thermoplastic or thermosetting resin is blended with inorganic fillers such as glass fibers, silica, talc and the like, the resin can exhibit improved properties such as tear strength, tensile strength, flexural strength, flexural modulus and the like, due to inherent properties of the inorganic fillers. Typically, blends of the thermoplastic resin, such as polycarbonates and the like, with the inorganic fillers are used for molded articles requiring high stiffness, and particularly for interior/exterior materials of automobiles and electronic products.

However, when the thermoplastic resin is blended with the inorganic fillers, the thermoplastic resin can suffer from reduction in molecular weight due to decomposition of the resin, and a molded article prepared using the blend can suffer from deterioration in appearance due to protrusion of the inorganic fillers from a surface of the molded article.

To solve such problems, a material capable of controlling interface properties between the thermoplastic resin and the fillers is typically used. Such materials include surfactants, coupling agents and the like. The interface properties can be controlled such that one end of the material reacts with the thermoplastic resin and the other end thereof reacts with the fillers. If the interface properties can be controlled, the resin can exhibit improved impact strength and the like.

US Patent Publication No. 2012-0245262 discloses a polycarbonate composition using a sulfonate and inorganic fillers to improve impact properties. EP 1860145 discloses a polysulfone composition including fibrous (acicular) fillers and a sulfonate to improve impact properties.

However, there is a limit in improvement of impact resistance of blends of a polycarbonate resin and the inorganic fillers when the surfactant, the coupling agent or the like is used alone, and there is also a limit in preventing reduction in molecular weight of the polycarbonate resin.

Therefore, there is a need for a polycarbonate resin composition that secures excellent impact resistance with minimal or no reduction in molecular weight of the polycarbonate resin, and a molded article including the polycarbonate resin composition.

SUMMARY

The present invention can provide a novel silane compound, a method for preparing the silane compound, a polycarbonate resin composition that includes the silane compound and can secure excellent impact resistance with minimal or no reduction in molecular weight of a polycarbonate resin, and a molded article including the resin composition.

The silane compound is represented by Formula 1:

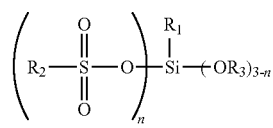

[Formula 1]

wherein $R_1$ is $C_6$ to $C_{30}$ alkyl; $R_2$ is a $C_6$ to $C_{30}$ hydrocarbon group; $R_3$ is hydrogen or $C_1$ to $C_5$ alkyl; and n has an average value from about 0.1 to about 3.

The present invention also relates to a method for preparing the silane compound. The method includes: reacting a silane compound represented by Formula 2 with a sulfonic acid compound represented by Formula 3:

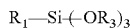

[Formula 2]

wherein $R_1$ and $R_3$ are defined as in Formula 1;

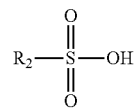

[Formula 3]

wherein $R_2$ is defined as in Formula 1.

In one embodiment, a mole ratio of the silane compound to the sulfonic acid compound may range from about 1:0.1 to about 1:3.

In one embodiment, reaction may be performed at about 10° C. to about 150° C.

The present invention also relates to a polycarbonate resin composition. The polycarbonate resin composition includes: a polycarbonate resin; an inorganic filler; and the silane compound represented by Formula 1, wherein the inorganic filler includes talc.

In one embodiment, the inorganic filler may further include at least one of silica, glass fibers, mica, wollastonite, basalt fibers, and whiskers.

In one embodiment, the inorganic filler may be present in an amount of about 5 parts by weight to about 70 parts by weight based on about 100 parts by weight of the polycarbonate resin, and the silane compound may be present in an amount of about 0.1 parts by weight to about 7 parts by weight based on about 100 parts by weight of the polycarbonate resin.

In one embodiment, a ratio of the inorganic filler to the silane compound (weight ratio, inorganic filler:silane compound) may range from about 10:1 to about 50:1.

In one embodiment, the polycarbonate resin composition may have an Izod impact strength from about 8.9 kgf·cm/cm to about 20 kgf·cm/cm, as measured on an about ⅛" thick specimen in accordance with ASTM D256; a falling dart impact (FDI) strength from about 19 J to about 40 J, as measured on an about 1 mm thick specimen in accordance with the DuPont drop measurement method; and a melt flow index (MI) from about 10 g/10 min to about 80 g/10 min, as measured in accordance with ASTM D1238.

The present invention further relates to a method for preparing the polycarbonate resin composition. The method includes mixing and reacting a polycarbonate resin, an inorganic filler, the silane compound represented by Formula 2, and the sulfonic acid compound represented by Formula 3 at about 10° C. to about 150° C., wherein the inorganic filler includes talc.

The present invention also relates to a molded article formed from the polycarbonate resin composition.

DETAILED DESCRIPTION

Exemplary embodiments now will be described more fully hereinafter in the following detailed description, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

According to one embodiment of the present invention, a silane compound is represented by Formula 1:

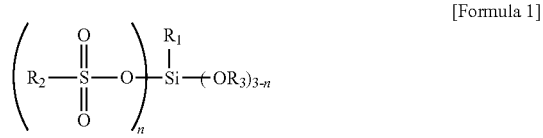

[Formula 1]

wherein $R_1$ may be $C_6$ to $C_{30}$ alkyl, for example, $C_6$ to $C_{20}$ alkyl, and as another example hexyl, heptyl, octyl, 2-ethylhexyl, decyl, dodecyl, tetradecyl, and the like; $R_2$ may be a $C_6$ to $C_{30}$ hydrocarbon group, for example, $C_6$ to $C_{20}$ alkyl, $C_7$ to $C_{25}$ alkylaryl or arylalkyl and the like, and as another example $C_6$ to $C_{10}$ aryl substituted with $C_6$ to $C_{15}$ alkyl, such as dodecylphenyl(alkyl aryl), and the like; $R_3$ may be hydrogen or $C_1$ to $C_5$ alkyl, for example, methyl, ethyl, propyl, butyl or pentyl, and as another example methyl, ethyl, and the like; and n may have an average value from about 0.1 to about 3, for example, from about 0.2 to about 2. That is, the silane compound may have a structure in which the silane compounds having n of 0.1, 2 and/or 3 are mixed such that n has an average value from about 0.1 to about 3.

In one embodiment, the silane compound may be prepared by reacting a silane compound represented by Formula 2 with a sulfonic acid compound represented by

[Formula 2]

wherein $R_1$ and $R_3$ are defined as in Formula 1.

[Formula 3]

wherein $R_2$ is defined as in Formula 1.

Examples of the silane compound represented by Formula 2 may include without limitation decyltrimethoxysilane, decyltriethoxysilane, heptyltrimethoxysilane, heptyltriethoxysilane, octyltrimethoxysilane, octyltriethoxysilane, dodecyltrimethoxysilane, dodecyltriethoxysilane, and the like, and mixtures thereof.

Examples of the sulfonic acid compound represented by Formula 3 may include without limitation dodecylbenzenesulfonic acid, decylbenzenesulfonic acid, octadecylbenzenesulfonic acid, hexylsulfonic acid, heptylsulfonic acid, octylsulfonic acid, decylsulfonic acid, octadecylsulfonic acid, and the like, and mixtures thereof.

In one embodiment, although it can vary with an average value of n of the silane compound to be prepared, a mole ratio of the silane compound to the sulfonic acid compound (Formula 2:Formula 3) may range from about 1:0.1 to about 1:3, for example, from about 1:0.2 to about 1:2. Within this content range of the silane compound and the sulfonic acid compound, a polycarbonate resin composition including the silane compound of Formula 1 prepared using the silane compound of Formula 2 and the sulfonic acid of Formula 3 can exhibit excellent impact resistance with minimal or no reduction in molecular weight of the polycarbonate resin.

In one embodiment, the reaction may be performed at a temperature from about 10° C. to about 150° C., for example, from about 30° C. to about 120° C., and as another example from about 50° C. to about 110° C., for example, for about 1 hour to about 48 hours while stirring the mixture. In addition, to remove $R_3OH$ generated as reaction by-products, distillation, vacuum distillation and/or enrichment by volatilization may be performed. Within this range of reaction conditions, the silane compound can be prepared at high yield (about 90% or more).

In addition, the reaction may be performed in the presence of an organic solvent. Examples of the organic solvent may include without limitation toluene, benzene, ethyl ether, hexane, chlorobenzene, acetonitrile, tetrahydrofuran, and the like, and mixtures thereof. In some embodiments, the organic solvent may be a dehydrated organic solvent to prevent hydrolysis, without being limited thereto. When the organic solvent is a non-dehydrated organic solvent, —$OR_3$ in Formula 1 is substituted with a hydroxyl group or forms a condensate through hydrolysis, thereby providing a material having a structure of Si—OH or Si—O—Si.

The organic solvent may be present in an amount of about 10 parts by weight to about 100 parts by weight based on about 100 parts by weight of the silane compound represented by Formula 2 and the sulfonic acid compound represented by Formula 3, without being limited thereto.

According to the present invention, a polycarbonate resin composition includes a polycarbonate resin, an inorganic filler, and the silane compound represented by Formula 1.

According to the present invention, the polycarbonate resin is a typical thermoplastic polycarbonate resin. For example, the polycarbonate resin may be an aromatic polycarbonate resin prepared by reacting one or more diphenols (aromatic diol compounds) with a precursor such as phosgene, halogen formates, diaryl carbonates, and the like.

Examples of diphenols may include without limitation 4,4'-biphenol, 2,2-bis(4-hydroxyphenyl)propane, 2,4-bis(4-hydroxyphenyl)-2-methylbutane, 1,1-bis(4-hydroxyphenyl)cyclohexane, 2,2-bis(3-chloro-4-hydroxyphenyl)propane, 2,2-bis(3,5-dichloro-4-hydroxyphenyl)propane, and the like, and mixtures thereof. For example, the diphenol may include 2,2-bis(4-hydroxyphenyl)propane, 2,2-bis(3,5-dichloro-4-hydroxyphenyl)propane, and/or 1,1-bis(4-hydroxyphenyl)cyclohexane, for example 2,2-bis(4-hydroxyphenyl)propane, which is also referred to as bisphenol-A.

The polycarbonate resin may be a branched polycarbonate resin and may be prepared by, for example, adding about 0.05 mol % to about 2 mol % of a polyfunctional compound containing tri- or higher functional groups, for example, tri or higher-valent phenol groups, based on the total amount of diphenols used in polymerization.

The polycarbonate resin may be used in the form of a homo-polycarbonate resin, a co-polycarbonate resin, or blends thereof.

In addition, the polycarbonate resin may be partially or completely replaced by an aromatic polyester-carbonate resin obtained by polymerization in the presence of an ester precursor, for example, a bifunctional carboxylic acid.

The polycarbonate resin may have a weight average molecular weight (Mw) from about 10,000 g/mol to about 200,000 g/mol, for example, from about 15,000 g/mol to about 80,000 g/mol, without being limited thereto.

According to the present invention, the inorganic filler includes talc, and may be talc alone or a mixture of talc and other inorganic fillers.

The talc may be any talc used for typical thermoplastic resin compositions without limitation. For example, flake fillers have a thin film shape, a z-axis length (thickness) which is smaller than a sectional area defined by x-axis and y-axis lengths. In addition, the flake fillers may have an average thickness from about 30 nm to about 700 nm, for example, from about 30 nm to about 300 nm, and as another example from about 32 nm to about 270 nm; an average particle size from about 0.65 μm to about 5.0 μm, for example, from about 0.65 μm to about 2.7 μm, and as another example from about 0.8 μm to about 2.5 μm; and a ratio of the average diameter (average x-axis or y-axis length) to the average thickness (z-axis length) (aspect ratio, diameter/thickness) from about 4 to about 30, for example, from about 10 to about 30. As the ratio of the average diameter to the average thickness increases, stiffness of the polycarbonate resin composition increases. For reference, the average particle size of the flake fillers refers to a median value of particle size distribution measured by X-ray transmission. Specifically, the particle size distribution of the flake fillers are obtained by X-ray transmission of sinking particles, followed by calculating the median value, thereby obtaining the average particle size.

In one embodiment, the inorganic filler other than talc may include inorganic fillers for typical thermoplastic resin compositions. Examples of the inorganic filler other than talc may include without limitation silica, glass fibers, mica, wollastonite, basalt fibers, whiskers, and the like, and mixtures thereof. Examples of whiskers may include without limitation potassium titanate whiskers, magnesium sulfate whiskers, calcium carbonate whiskers, aluminum borate whiskers, and the like, and mixtures thereof. In addition, the glass fibers may include glass fiber reinforcing agents in which fibers are formed by bundling glass filaments coated with a sizing agent such as epoxy, urethane, silane and the like, without being limited thereto. Here, the sizing agent may be present in an amount of about 0.05 parts by weight to about 2.0 parts by weight based on about 100 parts by weight of the glass filaments, without being limited thereto.

The inorganic filler may include talc alone, or may include talc in combination with another inorganic filler. In some embodiments, the inorganic filler may include talc in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 wt %. Further, according to some embodiments of the present invention, the amount of talc can be in a range from about any of the foregoing amounts to about any other of the foregoing amounts.

For example, in exemplary embodiments, the inorganic filler may include talc in an amount of about 14% by weight (wt %) to about 100 wt %, for example, about 15 wt % to about 60 wt %, and as another example about 20 wt % to about 35 wt % based on the total amount (total weight, 100 wt %) of the inorganic filler.

The inorganic filler may optionally include the inorganic filler other than talc in an amount of about 86 wt % or less, for example, about 40 wt % to about 85 wt %, and as another example about 65 wt % to about 80 wt % based on the total amount (total weight, 100 wt %) of the inorganic filler. In some embodiments, the inorganic filler may include the inorganic filler other than talc in an amount of 0 (the inorganic filler other than talc is not present), about 0 (the inorganic filler other than talc is present), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, or 86 wt %. Further, according to some embodiments of the present invention, the amount of the inorganic filler other than talc can be in a range from about any of the foregoing amounts to about any other of the foregoing amounts.

Within these ranges, the polycarbonate resin composition can secure excellent impact resistance with minimal or no reduction in molecular weight of the polycarbonate resin.

In one embodiment, the polycarbonate resin composition may include inorganic filler in an amount of about 5 parts by weight to about 70 parts by weight, for example, about 10 parts by weight to about 50 parts by weight, based on about 100 parts by weight of the polycarbonate resin. In some embodiments, the polycarbonate resin composition may include inorganic filler in an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 parts by weight. Further, according to some embodiments of the present invention, the amount of the inorganic filler can be in a range from about any of the foregoing amounts to about any other of the foregoing amounts.

Within this range, the polycarbonate resin composition can secure excellent impact resistance with minimal or no reduction in molecular weight of the polycarbonate resin.

According to the present invention, the silane compound represented by Formula 1 serves as a compatibilizer or a coupling agent in the polycarbonate resin composition, and thus can improve adhesion between the polycarbonate resin and the inorganic filler and improve impact resistance of the resin composition with minimal or no reduction in molecular weight of the polycarbonate resin.

In exemplary embodiments, the silane compound may be used through refinement, or may be used for the polycarbonate resin composition in the form of a mixture including an organic solvent used in the preparation of the silane compound.

In exemplary embodiments, the polycarbonate resin composition may include the silane compound in an amount of about 0.1 parts by weight to about 7 parts by weight, for example, about 0.5 parts by weight to about 5 parts by weight, based on about 100 parts by weight of the polycarbonate resin. In some embodiments, the polycarbonate resin composition may include the silane compound in an amount of about 0.1, 0.2, 0.3, 0.4, 0.5, 0.6, 0.7, 0.8, 0.9, 1, 2, 3, 4, 5, 6, or 7 parts by weight. Further, according to some embodiments of the present invention, the amount of the silane compound can be in a range from about any of the foregoing amounts to about any other of the foregoing amounts.

Within this range, the polycarbonate resin composition can secure excellent impact resistance with minimal or no reduction in molecular weight of the polycarbonate resin.

In one embodiment, a ratio of the inorganic filler to the silane compound (weight ratio, inorganic filler:silane compound) may range from about 10:1 to about 50:1, for example, from about 20:1 to about 40:1. Within this range, the polycarbonate resin composition can secure excellent impact resistance with minimal or no reduction in molecular weight of the polycarbonate resin.

According to the present invention, the polycarbonate resin composition may further include one or more additives, as needed. Examples of the additives may include without limitation flame retardants, flame retardant aids, lubricants, plasticizers, heat stabilizers, anti-dripping agents, antioxidants, photostabilizers, pigments, dyes, and the like. These additives may be used alone or in combination thereof. For example, the additives may be present in an amount of about 0.1 parts by weight to about 10 parts by weight, based on about 100 parts by weight of the polycarbonate resin, without being limited thereto.

According to the present invention, the polycarbonate resin composition may be prepared by: (a) mixing the above components; or (b) adding the silane compound represented by Formula 1 in the form of a mixture of the silane compound represented by Formula 2 and the sulfonic acid compound represented by Formula 3, followed by mixing and reaction at about 10° C. or more, for example, at about 10° C. to about 150° C.

In addition, the polycarbonate resin composition may be prepared in pellet form through melt extrusion of the mixture or the mixed reaction product at about 200° C. to about 280° C. for example, about 250° C. to about 260° C. using a typical twin-screw extruder. At this extrusion temperature, a silane group of the silane compound and a hydroxyl group of the inorganic filler can form a covalent bond through condensation on the surfaces of the inorganic filler and form a chemical bond through dehydration-condensation in the process of extrusion and drying.

The pellets may be formed into various molded articles through various molding methods such as injection molding, extrusion, vacuum molding, cast molding, and the like. These molding methods are well known by those of ordinary skill in the art.

In one embodiment, the polycarbonate resin composition according to the present invention may have an Izod impact strength from about 8.9 kgf·cm/cm to about 20 kgf·cm/cm, for example, from about 9 kgf·cm/cm to about 16 kgf·cm/cm, as measured on an about ⅛" thick specimen in accordance with ASTM D256.

The polycarbonate resin composition may have a falling dart impact (FDI) strength (crack generation energy) from about 19 J to about 40 J, for example, from about 20 J to about 35 J, as measured on an about 1 mm thick specimen (about 10 cm×about 10 cm×about 1 mm) using an about 2 kg dart in accordance with the DuPont drop measurement method, in which a maximum height not generating a crack is measured by adjusting a height of the dart, followed by converting the maximum height into potential energy. Here, the maximum height is obtained in such a manner that a dart having a certain weight is dropped onto the about 1 mm thick specimen from a varying height, followed by observing generation of cracks in the specimen by the naked eye.

In addition, the polycarbonate resin composition may have a melt flow index (MI) from about 10 g/10 min to about 80 g/10 min, for example, from about 15 g/10 min to about 60 g/10 min, as measured in accordance with ASTM D1238.

According to the present invention, a molded article can be formed from the polycarbonate resin composition through various molding methods. Since the molded article can exhibit excellent impact resistance, the molded article can be useful for interior/exterior materials of electronic products, such as mobile devices, notebook computers, monitors, TVs, and the like.

Hereinafter, the present invention will be described in more detail with reference to the following examples. It should be understood that these examples are provided for illustration only and are not to be construed in any way as limiting the present invention. A description of details apparent to those skilled in the art will be omitted for clarity.

EXAMPLE

Preparative Example 1

Preparation of Silane Compound

A silane compound (decyltrimethoxysilane) represented by Formula 2a and a sulfonic acid compound (dodecylbenzenesulfonic acid) represented by Formula 3a are added to toluene as a solvent in a mole ratio of 1:0.19 (Formula 2a:Formula 3a), followed by refluxing at 110° C. for 2 hours, thereby preparing a silane compound represented by Formula 1a (average value of n: 0.19). Synthesis of the prepared silane compound and the average value of n are checked using $^1$H-NMR and Si-NMR spectra.

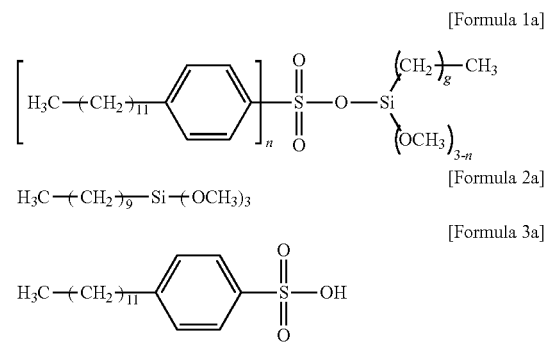

[Formula 1a]

[Formula 2a]

[Formula 3a]

Preparative Example 2

Preparation of Silane Compound

A silane compound (decyltrimethoxysilane) represented by Formula 2a and a sulfonic acid compound (dodecylbenzenesulfonic acid) represented by Formula 3a are added to toluene as a solvent in a mole ratio of 1:0.51 (Formula 2a:Formula 3a), followed by refluxing at 110° C. for 2 hours, thereby preparing a silane compound represented by Formula 1a (average value of n: 0.51). Synthesis of the prepared silane compound and the average value of n are checked using $^1$H-NMR and Si-NMR spectra.

Preparative Example 3

Preparation of Silane Compound

A silane compound (decyltrimethoxysilane) represented by Formula 2a and a sulfonic acid compound (dodecylbenzenesulfonic acid) represented by Formula 3a are added to toluene as a solvent in a mole ratio of 1:0.77 (Formula 2a:Formula 3a), followed by refluxing at 110° C. for 2 hours, thereby preparing a silane compound represented by Formula 1a (average value of n: 0.77). Synthesis of the prepared silane compound and the average value of n are checked using $^1$H-NMR and Si-NMR spectra.

Preparative Example 4

Preparation of Silane Compound

A silane compound (decyltrimethoxysilane) represented by Formula 2a and a sulfonic acid compound (dodecylbenzenesulfonic acid) represented by Formula 3a are added to toluene as a solvent in a mole ratio of 1:1.16 (Formula 2a:Formula 3a), followed by refluxing at 110° C. for 2 hours, thereby preparing a silane compound represented by Formula 1a (average value of n: 1.16). Synthesis of the prepared silane compound and the average value of n are checked using $^1$H-NMR and Si-NMR spectra.

Preparative Example 5

Preparation of Silane Compound

A silane compound (decyltrimethoxysilane) represented by Formula 2a and a sulfonic acid compound (dodecylbenzenesulfonic acid) represented by Formula 3a are added to toluene as a solvent in a mole ratio of 1:0.56 (Formula 2a:Formula 3a), followed by refluxing at 110° C. for 2 hours, thereby preparing a silane compound represented by Formula 1a (average value of n: 0.56). Synthesis of the prepared silane compound and the average value of n are checked using $^1$H-NMR and Si-NMR spectra.

Details of components used in Examples and Comparative Examples are as follows.

(A) Polycarbonate Resin

Bisphenol-A polycarbonate (SC-1190G, Cheil Industries Inc., weight average molecular weight: 25,300 g/mol, melt flow index (MI, measured at 300° C. under a load of 1.2 kg in accordance with ISO 1133): 20 g/10 min) is used.

(B) Inorganic Filler

Talc (KC-3000, KOCH Co., Ltd.) is used.

(C) Silane Compound

Silane compounds of Preparative Examples 1 to 5 ((C1) to (C5)) are used.

(D) Silane Compound

Decyltrimethoxysilane (KBM3103C, Shin-Etsu Chemical Co., Ltd.) is used.

(E) Sulfonic Acid Compound

Dodecylbenzenesulfonic acid (Dodecyl benzene sulfonic acid, Daejung Chemicals & Metals Co. Ltd., EP grade, 95%) is used.

(F) Sulfonate

Sodium dodecylbenzenesulfonate (D0990, TCI Co., Ltd.) is used.

Examples 1 to 5 and Comparative Examples 1 to 5

The components are added in amounts as listed in Tables 2 and 3, respectively, followed by extrusion at 200° C. to 280° C., thereby preparing pellets. Extrusion is performed using a twin-screw extruder having L/D=36 and a diameter of 45 mm. The prepared pellets are dried at 80° C. to 100° C. for 4 hours or more, followed by injection molding in a 6 oz injection machine (molding temperature: 280° C., mold temperature: 60° C.), thereby preparing specimens. Each of the prepared specimens is evaluated as to the following properties. Results are shown in Tables 2 and 3.

Evaluation of Properties (1) Izod impact strength (unit: kgf·cm/cm): Izod impact strength is measured on a 1/8" thick notched Izod specimen in accordance with ASTM D256.

(2) Falling dart impact (FDI) strength (unit: J): FDI strength is measured by measuring a height generating a crack in a 1.0 mm thick specimen (10 cm×10 cm×1 mm) using a 2 kg dart in accordance with the DuPont drop measurement method, followed by converting the height into energy.

(3) Melt flow index (MI, unit: g/10 min): Melt flow index is measured at 300° C. under a load of 5 kg in accordance with ASTM D1238.

(4) Weight average molecular weight (Mw, unit: g/mol): A weight average molecular weight of the polycarbonate resin included in the injection-molded specimen is determined by dissolving 0.01 g of the resin specimen in 2 ml of dichloromethane, diluting the solution with 10 ml of tetrahydrofuran, followed by filtering the resultant material using a 0.45 μm syringe filter to obtain samples. Then, the obtained samples are analyzed using the following apparatuses, conditions and polystyrene standard samples (eight types of SM-105, Shodex Co., Ltd.).

TABLE 1

| System | Waters 515 HPLC pump |
|---|---|
| | Waters 2414 RI detector |
| | Waters 717 plus auto sampler |
| Column | Shodex LF-804 2EA(8.0.1.D. × 300 mm) |
| Flow rate (ml/min) | 1 |
| Pressure (psi) | 645 |
| Solvent | THF |
| Injection volume (μl) | 200 |
| Oven temperature | 35° C. |

TABLE 2

| | Example | | | | |
|---|---|---|---|---|---|
| | 1 | 2 | 3 | 4 | 5 |
| (A) (parts by weight) | 100 | 100 | 100 | 100 | 100 |
| (B) (parts by weight) | 25 | 25 | 25 | 25 | 25 |
| (C) (C1) (parts by weight) | 0.625 | — | — | — | — |
| (C2) (parts by weight) | — | 0.625 | — | — | — |
| (C3) (parts by weight) | — | — | 0.625 | — | — |
| (C4) (parts by weight) | — | — | — | 0.625 | — |
| (C5) (parts by weight) | — | — | — | — | 1.0625 |
| (D) (parts by weight) | — | — | — | — | — |
| (F) (parts by weight) | — | — | — | — | — |
| Izod impact, strength | 9.0 | 9.8 | 10.2 | 10.6 | 12.7 |
| FDI strength | 20 | 24 | 32 | 32 | 32 |
| Melt flow index | 22 | 21 | 19 | 20 | 22 |
| Weight average molecular weight | 25,100 | 25,300 | 25,300 | 25,100 | 25,000 |

TABLE 3

|  | Comparative Example | | | | |
| --- | --- | --- | --- | --- | --- |
|  | 1 | 2 | 3 | 4 | 5 |
| (A) (parts by weight) | 100 | 100 | 100 | 100 | 100 |
| (B) (parts by weight) | 25 | 25 | 25 | 25 | 25 |
| (D) (parts by weight) | — | 0.625 | — | 0.3125 | — |
| (E) (parts by weight) | — | — | 0.625 | — | — |
| (F) (parts by weight) | — | — | — | 0.3125 | 0.625 |
| Izod impact strength | 3.6 | 6.9 | 6.8 | 8.7 | 8.5 |
| FDI strength | 5 | 18 | 8 | 18 | 18 |
| Melt flow index | 290 | 28 | 41 | 24 | 27 |
| Weight average molecular weight | 16,300 | 25,300 | 19,400 | 24,900 | 21,400 |

From the results, it can be seen that the polycarbonate resin compositions according to the present invention (Examples 1 to 5) scarcely suffered from reduction in weight average molecular weight and exhibit excellent impact strength (Izod, FDI).

Conversely, it can be seen that the polycarbonate resin compositions of Comparative Examples 1, 3 and 5 suffer from deterioration in impact strength (Izod, FDI) as compared with those of Examples, since the polycarbonate resin is decomposed by the inorganic filler (talc), the sulfonic acid (dodecylbenzenesulfonic acid) and/or the sulfonate (sodium dodecylbenzenesulfonate). It can be seen that, although the polycarbonate resin composition of Comparative Example 4, in which the silane compound and the sulfonate are used without reaction, did not significantly suffer from decomposition of the polycarbonate resin, the polycarbonate resin composition of Comparative Example 4 suffers from deterioration in impact strength (Izod, FDI) as compared with those of Examples. In addition, it can be seen that the polycarbonate resin composition of Comparative Example 2, in which the silane compound is used alone, did not suffer from decomposition of the polycarbonate resin, the polycarbonate resin composition of Comparative Example 2 suffers from deterioration in impact strength (Izod, FDI) as compared with those of Examples.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims.

What is claimed is:

1. A silane compound represented by Formula 1:

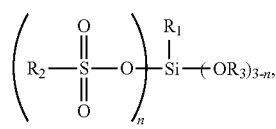

[Formula 1]

wherein $R_1$ is $C_6$ to $C_{30}$ alkyl, $R_2$ is a $C_6$ to $C_{30}$ hydrocarbon group, $R_3$ is hydrogen or $C_1$ to $C_5$ alkyl, and n has an average value from about 0.1 to about 3.

2. A method for preparing a silane compound represented by Formula 1, comprising:
reacting a silane compound represented by Formula 2 with a sulfonic acid compound represented by Formula 3,

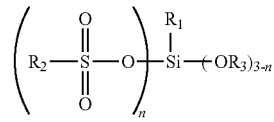

[Formula 1]

wherein $R_1$ is $C_6$ to $C_{30}$ alkyl, $R_2$ is a $C_6$ to $C_{30}$ hydrocarbon group, $R_3$ is hydrogen or $C_1$ to $C_5$ alkyl, and n has an average value from about 0.1 to about 3,

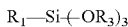

[Formula 2]

wherein $R_1$ and $R_3$ are defined as in Formula 1,

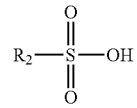

[Formula 3]

wherein $R_2$ is defined as in Formula 1.

3. The method according to claim 2, wherein a mole ratio of the silane compound to the sulfonic acid compound ranges from about 1:0.1 to about 1:3.

4. The method according to claim 2, wherein the reaction is performed at a temperature from about 10° C. to about 150° C.

5. A polycarbonate resin composition comprising:
a polycarbonate resin;
an inorganic filler, wherein the inorganic filler comprises talc; and
a silane compound represented by Formula 1,

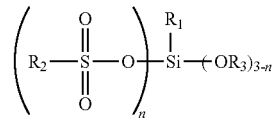

[Formula 1]

wherein $R_1$ is $C_6$ to $C_{30}$ alkyl, $R_2$ is a $C_6$ to $C_{30}$ hydrocarbon group, $R_3$ is hydrogen or $C_1$ to $C_5$ alkyl, and n has an average value from about 0.1 to about 3.

6. The polycarbonate resin composition according to claim 5, wherein the inorganic filler further comprise silica, glass fibers, mica, wollastonite, basalt fibers, whiskers, or a mixture thereof.

7. The polycarbonate resin composition according to claim 5, comprising the inorganic filler in an amount of about 5 parts by weight to about 70 parts by weight based on about 100 parts by weight of the polycarbonate resin, and comprising the silane compound in an amount of about 0.1 parts by weight to about 7 parts by weight based on about 100 parts by weight of the polycarbonate resin.

8. The polycarbonate resin composition according to claim 5, comprising a ratio of the inorganic filler to the silane compound (weight ratio, inorganic filler:silane compound) of about 10:1 to about 50:1.

9. The polycarbonate resin composition according to claim 5, wherein the polycarbonate resin composition has an Izod impact strength from about 8.9 kgf·cm/cm to about 20 kgf·cm/cm, as measured on an about ⅛" thick specimen in accordance with ASTM D256, a falling dart impact (FDI) strength from about 19 J to about 50 J, as measured on an about 1 mm thick specimen in accordance with the DuPont drop measurement method, and a melt flow index (MI) from about 10 g/10 min to about 80 g/10 min, as measured in accordance with ASTM D1238.

10. A molded article formed from the polycarbonate resin composition according to claim 5.

11. A method for preparing a polycarbonate resin composition, comprising:

mixing a polycarbonate resin, an inorganic filler, wherein the inorganic filler comprises talc, and a silane compound represented by Formula 1,

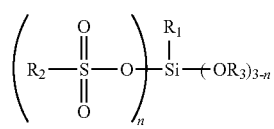

[Formula 1]

wherein $R_1$ is $C_6$ to $C_{30}$ alkyl, $R_2$ is a $C_6$ to $C_{30}$ hydrocarbon group, $R_3$ is hydrogen or $C_1$ to $C_5$ alkyl, and n has an average value from about 0.1 to about 3.

12. A method for preparing a polycarbonate resin composition, comprising:

mixing and reacting a polycarbonate resin, inorganic filler, wherein the inorganic filler comprises talc, a silane compound represented by Formula 2, and a sulfonic acid compound represented by Formula 3 at about 10° C. to about 150° C.,

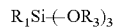

[Formula 2]

wherein $R_1$ is $C_6$ to $C_{30}$ alkyl and $R_3$ is $C_1$ to $C_5$ alkyl,

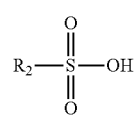

[Formula 3]

wherein $R_2$ is a $C_6$ to $C_{30}$ hydrocarbon group.

* * * * *

UNITED STATES PATENT AND TRADEMARK OFFICE
CERTIFICATE OF CORRECTION

PATENT NO. : 9,085,674 B2  
APPLICATION NO. : 14/537219  
DATED : July 21, 2015  
INVENTOR(S) : Yong Tae Kim et al.

Page 1 of 1

It is certified that error appears in the above-identified patent and that said Letters Patent is hereby corrected as shown below:

In the Specification

Column 8, Formula 1a is depicted as:

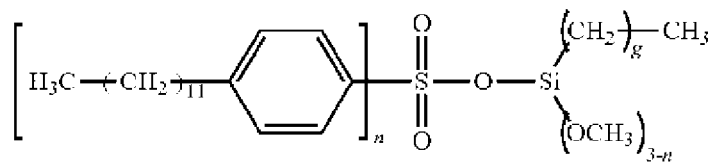

and should be depicted as:

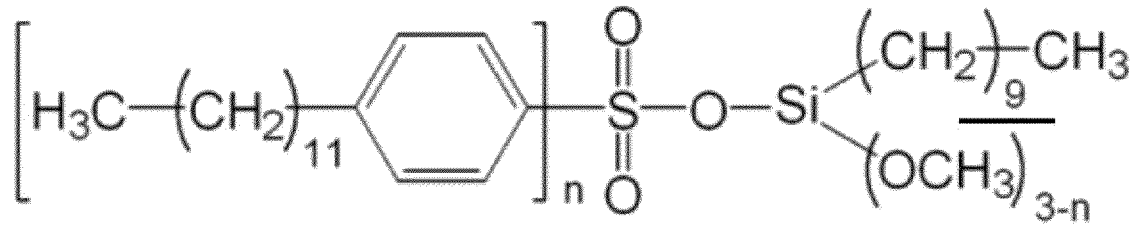

Signed and Sealed this  
Third Day of May, 2016

Michelle K. Lee  
*Director of the United States Patent and Trademark Office*